(12) United States Patent
Høier et al.

(10) Patent No.: US 7,018,664 B2
(45) Date of Patent: Mar. 28, 2006

(54) METHOD AND APPARATUS FOR PREPARING A DAIRY PRODUCT

(75) Inventors: Erik Høier, Valby (DK); Claus Michael Andersen, Farum (DK)

(73) Assignee: Chr. Hansen A/S, Horsholm (DK)

( * ) Notice: Subject to any disclaimer, the term of this patent is extended or adjusted under 35 U.S.C. 154(b) by 351 days.

(21) Appl. No.: 10/210,078

(22) Filed: Aug. 2, 2002

(65) Prior Publication Data

US 2003/0031755 A1    Feb. 13, 2003

Related U.S. Application Data

(60) Provisional application No. 60/309,489, filed on Aug. 3, 2001.

(30) Foreign Application Priority Data

Aug. 3, 2001    (DK)    ................................ 2001 01176

(51) Int. Cl.
    *A23C 9/12*    (2006.01)
(52) U.S. Cl. ........................... 426/34; 426/42; 426/43; 426/580
(58) Field of Classification Search .................. 426/34, 426/36, 42, 43, 580, 582, 583
    See application file for complete search history.

(56) References Cited

U.S. PATENT DOCUMENTS

| 3,017,274 A | 1/1962 | Dahlstrom |
| 4,544,636 A | 10/1985 | Bily |

FOREIGN PATENT DOCUMENTS

| EP | 0 061 946 A1 | 10/1982 |
| EP | 0 061 946 B1 | 10/1984 |
| FR | 2 409 011 | 6/1979 |
| WO | WO 99/09838 | 4/1999 |

OTHER PUBLICATIONS

Shirley Ho et al.; Feasibility of Continuous Yogurt Processing; Milchwissenschaft 50(3); pp. 146-150; 1995.
PCT International Search Report, PCT/DK 02/00503, Oct. 24, 2002.

*Primary Examiner*—Leslie Wong
(74) *Attorney, Agent, or Firm*—Hunton & Williams

(57) ABSTRACT

A novel method and apparatus are disclosed for the manufacturing of dairy products. Also dairy products prepared by means of the disclosed method are comprised by the invention. The novel method makes use of preactivated cultures and results in a reduction of production time and costs in addition to a less complicated planning of the production work.

17 Claims, 1 Drawing Sheet

METHOD AND APPARATUS FOR PREPARING A DAIRY PRODUCT

CROSS-REFERENCE TO RELATED APPLICATIONS

This application claims priority under 35 U.S.C. § 119 from Danish application PA 2001 01176, filed Aug. 3, 2001 and under 35 U.S.C. § 19(e) from U.S. patent application 60/309,489, filed on Aug. 3, 2001, the contents of both of which are incorporated herein by reference.

BACKGROUND OF THE INVENTION

1. Field of the Invention

This invention relates to methods and principles for apparatus for the manufacture of dairy products, from dairy starter cultures. Additionally, this invention relates to dairy products prepared by means of the disclosed method and apparatus and the use of the method and apparatus for manufacturing of dairy products.

2. Background

The preparation of most dairy products involves as a rule the use of microorganisms, in particular bacteria, such as e.g. lactic acid bacteria. Lactic acid bacteria are essential in the making of all fermented milk products, cheese and butter, and they are normally supplied to the dairy industry either as frozen or freeze-dried cultures for bulk starter propagation or as so-called "Direct Vat Set" (DVS) cultures, intended for direct inoculation to a fermentation vat for the dairy product.

In a commercial cheese production plant used at the present time, the time interval between successive inoculation of the culture into the cheese vats can typically vary from around 30 to 40 minutes in a large cheese plant with a vat size of around 26,000 liters, to only 1 to 2minutes in soft cheese production, using cheese vats of only around 200–300 liters in size.

A disadvantage by the use of pellets of frozen or freeze-dried DVS cultures, particularly with said small vat sizes, is that it requires a high degree of manual handling since the DVS culture has to be weighted out manually and then added separately to each cheese vat. Furthermore, because of a need for rapid filling and inoculation, particularly in soft cheese production, the manual addition of solid DVS cultures often presents a significant organisational and coordinational challenge regarding the planning of the working schedule for the staff, which eventually results in higher production costs.

WO-A-99/09838 describes a starter delivery system for direct and automatic dosage of DVS cultures in which the DVS culture is suspended in a water solution making a stable liquid culture suspension ready for direct inoculation into the cheese vat. However, although a stabilisation of the culture to be added is achieved the lag phase prior to growth is still unaltered and undesirably long.

In the production of different cheese types and fermented products there is a continuous need for very active cultures, in order to shorten the lag phase for fermentation in the production process, and thereby minimise the capacity cost for equipment.

Traditionally, high volumes of bulk starter cultures, typically constituting addition of 2–6% of the starter culture, have traditionally been employed, particularly in the production of e.g. set yoghurt and various soft cheeses, in order to e.g. shorten the lag phase. This also has the secondary effect of lowering the pH value of the milk immediately. However, the consequence of using said high dosage of bulk starter in combination with the slightly longer lag phase of DVS cultures, is obviously that the DVS cultures need a longer residence time when replacing the bulk starter with DVS cultures in production of dairy products. This is a problem in some production processes, because the required amount of DVS cultures is high implying relatively high production costs.

It is known from the prior art that DVS cultures can be pre-activated by blending the DVS culture with a small volume of preheated milk in a vessel or tank, and by pre-activating the culture for 30–60 min before addition to the cheese vat or the fermentation vessel. The preactivation is normally enabled by means of a range of vessels containing 20–50 liters of milk in which the DVS culture is added and kept for 30–60 minutes. Following an initial short period of incubation, the milk is ready for further inoculation of the cheese vat or fermentation tank over a period of time of 15–60 minutes. Normally, such systems are batch-type systems that frequently render significant variation in the pre-activation time between fills, which is a problem in the quality control work and the planning and management of the production work.

It appears from the above that there is a clear need in the market for a method and apparatus that diminish the inter batch quality variation of the products, shorten the production time for fermented dairy products, facilitate the planning and management of the production work and reduce the production costs.

SUMMARY

The inventors of the present invention have surprisingly found a novel method and a novel apparatus that meet these requirements. The present invention will be described below by disclosing a method and an apparatus in more detail.

According to a first aspect of the invention, a method is provided for preparation of a dairy product, comprising the steps of a) preparing an aqueous suspension of a dried or frozen microbial starter culture in pasteurised or sterile water;

b) providing a metered flow of the aqueous suspension and a metered flow of milk, and mixing the metered flow of the aqueous suspension with the metered flow of milk to form a milk/culture starter culture composition (or "starter culture composition");

c) passing the starter culture composition through an in-line pre-incubator, in which the starter culture composition is maintained at a preincubation temperature which is greater than about 10° C. (or greater than 10° C.), but not sufficiently high as to have a deleterious effect on the microbial culture, the preincubation temperature being from about 10° to about 50° C., preferably from about 20 to about 45° C., more preferably from about 30 to about 35° C., and wherein the residence time of the starter culture composition in the in-line pre-incubator is such as to pre-activate the starter culture composition to form an activated culture composition;

d) dispensing the activated culture composition into a fermentation vat together with an additional quantity of milk to provide a fermentation mixture; and e) maintaining the fermentation mixture under fermentation conditions to obtain the dairy product.

It is also possible to use a pre-incubator which is not an in-line pre-incubator. In such a case, the pre-incubator may include a vessel, a tank or a vat, which is not placed in-line, but is part of the apparatus used in the method of the invention.

The dried or frozen microbial starter culture may be a concentrated dried or frozen microbial starter culture. Pre-activation is in this context used interchangeably with pre-incubation, comprising also other grammatical forms of the words, such as e.g. nouns and verbs thereof, and is to be construed as a method that causes a state of activation prior to use, which implies a diminished lag phase preceding a growth phase. Methods of preactivation comprise a procurement of an appropriate ambience (or environment), such as e.g. an optimised temperature and humidity. Additionally, a suitable, e.g., an optimised, nutritional environment is also needed.

It appears that this novel method in which DVS cultures are pre-activated by blending with preheated milk in a controlled manner causes a decreased quality variation of the products compared with traditional batch production, results in a reduction of both production time and of costs in addition to a less complicated planning of the production work.

According to a second aspect of the invention, an apparatus is provided for activation of a concentrated starter culture for a dairy product, comprising the following elements:

a) a temperature-controlled mixing vessel, for preparing an aqueous suspension (or an "aqueous suspension product") of a dried or frozen microbial starter culture, including an inlet for sterile water, an inlet for the dried or frozen microbial starter culture, and an outlet for the aqueous suspension product, b) a means for forming a metered flow of the aqueous suspension, c) a means for producing a metered milk flow, d) a means for mixing the metered flow of the aqueous suspension with the metered milk flow, to form a milk/culture starter culture composition (or "starter culture composition"), e) an in-line pre-incubator, for the starter culture composition having a means for maintaining the starter culture composition at a preincubation temperature which is greater than 10° C. but not sufficiently high as to have a deleterious effect on the microbial culture, f) a means for introducing the starter culture composition (from the in-line incubator) into a fermentation vat for the production of a fermented milk product, at a rate allowing the residence time of the starter culture composition in the in-line preincubator to pre-activate the starter culture composition to form an activated culture composition.

The dried or frozen microbial starter culture may be a concentrated dried or frozen microbial starter culture.

The use of the pre-incubator facilitates the dispensation (or dispensing) of the microbial starter culture on demand, in a pre-incubated state, so that when it is introduced into milk in a fermentation vat, a reduced time is required for completion of the fermentation process. The advantages, which result from the use of dried or frozen microbial starters such as e.g. the ease of maintaining sterility, and the consistency of the starting material are not altered and therefore retained nonetheless.

DETAILED DESCRIPTION

Figure 1:
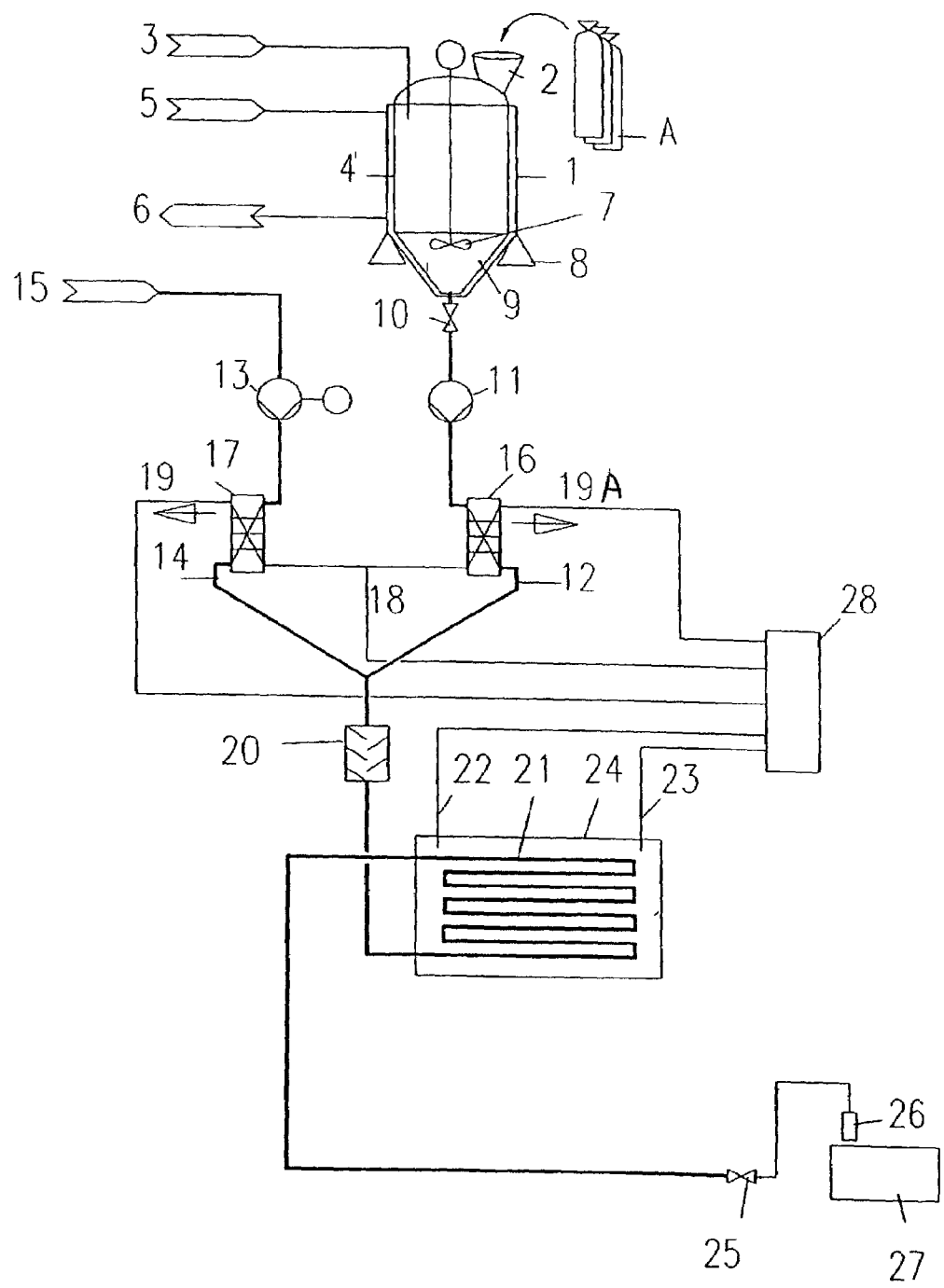
FIG. 1 is an illustration of one embodiment of the invention.

The residence time of the starter culture in the pre-incubator is preferably from about 10 to about 60 minutes, more preferably from about 10 to about 30 minutes and the temperature of the pre-incubator is from about 10 to about 50° C., preferably about 20 to about 45° C., more preferably from about 30 to about 35° C., although this will depend on the characteristics of the microorganism in question. The aqueous suspension of dried or frozen starter culture is prepared at a temperature of about 20° C. or less, preferably about 15° C. or less. In one embodiment, the residence time of the starter culture in the pre-incubator is from 10 to 60 minutes, preferably from 10 to 30 minutes and the temperature of the pre-incubator is from 10 to 50° C., preferably 20 to 45° C., more preferably 30 to 35° C., although, again, it will depend the characteristics of the microorganism in question.

The mixing of the aqueous suspension of starter culture composition with the metered flow of milk may preferably be carried out in a mixer connected directly to the pre-incubator, at the preincubation temperature. The pre-incubator and preferably the mixer may be maintained at preincubation temperature by surrounding it with a heated fluid, for example a water bath at the appropriate temperature. The activated culture composition may be dispensed at intervals of, for example, five minutes or less, preferably two minutes or less. Using the method of the invention, it is possible at determined points of time to dose small cheese vats of 100 to 2000 liters, preferably 150 to 1500 liters, more preferably from 200 to 1000 liters with pre-activated starter culture composition (i.e., the activated culture composition) in a very convenient manner.

In order to more fully understand the principles and aspects of the present invention, a detailed description of a preferred embodiment thereof will be given below. An example of such a preferred embodiment of the invention is shown in the accompanying drawing, which is a schematic representation of an apparatus and method for preparing a dairy product, in accordance with the invention.

FIG. 1 depicts an apparatus for preparing a starter culture that comprises DVS bags (A), a mixing vessel (1) having an inlet hopper (2) for a dried or frozen microbial starter culture, which may be a concentrated microbial starter culture.

A volume of pasteurised or sterile water constituting approximately 80% by volume of the resulting aqueous suspension in vessel (1) is supplied to the vessel (1) through an inlet (3). The vessel (1) is maintained at a constant temperature of approximately 15° C. or below, by means of a water jacket (4), connected to an inlet (5) and outlet (6) for cooling water. The contents of the vessel (1) may be agitated by means of a paddle (7), and a load cell (8) is provided to enable constant monitoring of the weight of the vessel, the contents of water and culture to achieve a correct blending ratio thereof. A temperature sensor (9) is also provided, connected to a temperature controller (not shown) to enable the temperature of the vessel to be monitored and controlled at approximately 15° C. or below.

The aqueous suspension of microbial starter culture prepared in vessel (1) is continuously (i.e., substantially) in a steady state of no growth, both because of the low temperature, and because of the absence of suitable nutrient media. It can be safely stored for up to 24 hours without significant reduction of activity. The suspension exits vessel (1) by means of an outlet valve (10).

On the one side, a metering/dosing system consisting of a pump (11) and a conduit (12) supplies the downstream side of the preactivation system with the DVS suspension at an appropriate rate. On the other side, pasteurised milk (15) at an appropriate rate is being supplied by means of a similar and parallel metering system with a pump (13) and a conduit (14) to the downstream side of the preactivation system. The flows of the DVS suspension and pasteurised milk are heated in Plate Heat Exchangers (PHE) (16) and (17), respectively. The DVS suspension and pasteurised milk are each heated to at a temperature of approximately 30° C., by means of a warm water circulation system (28) to the Plate Heat Exchangers (16) and (17), respectively.

Temperatures of from 20 to 45° C. are frequently chosen, but this can normally be further optimised to comply more fully with the type of culture and the particular application in question.

In the embodiment shown in FIG. 1, the PHEs (16) and (17) have a common water inlet (18) and two separate water outlets (19 and 19A). The PHEs (16) and (17) are designed in such a way that the plate areas are very large and the difference between the water in and outlet temperature is very low, such as e.g., approximately 1° C., which implies an almost constant temperature of the DVS suspension and pasteurised milk, regardless of the flow conditions in (16) and (17) comprising no flow, low flow or high flow. The flows of the DVS suspension including the microbial starter culture and pre-heated pasteurised milk are subsequently combined in an in-line mixer (20), and then passed as a homogeneous liquid mixture to an in-line pre-incubator (24), comprising an in-line tubular holding cell (21) and a heat exchanger (not illustrated).

In the in-line pre-incubator (24) the mixture is kept at a desired temperature and for a desired time. The in-line holding cell (21) is surrounded by a water bath, using the same warm water circulation as for the PHEs (16) and (17), whereby the temperatures in the PHEs (16) and (17) and in (21) are maintained at the same level. The warm water circulation has an inlet connection (22) and an outlet connection (23) to the in-line pre-incubator (24). The mixture inlet from the in-line mixer (20) for the in-line holding cell (21) is in the bottom part of the cell, so that air is evacuated in a controlled manner during initial filling of the holding cell. The in-line holding cell (21) is designed to allow for plug flow conditions to be achieved during operation.

Finally, the mixture is passed to a dosing valve (25) and dosing/dispensing nozzle (26), which enables selected quantities of the preincubation mixture to be dispensed into a cheese vat (27).

The physical preactivation system is designed to comply with high hygienic requirements, and is provided with means (not shown) for cleaning-in-place (CIP) and steaming-in-place (SIP) of generally conventional type.

A controller (not shown) of generally conventional form and type controls and monitors various parts and parameters of the preactivation system, such as e.g. the mechanical components and selected process parameters comprising inter alia (i.a.) the preactivation time and the temperature, the dispensing volume, the mixing ratio between milk and the DVS suspension.

In the embodiment shown in FIG. 1, the cheese vat (27) has a volume of around 1000 liters, and the dispenser nozzle (26) is capable of dispensing approximately 7 liters of the activated culture composition, in a period of from 10 to 20 seconds.

The method and apparatus according to the invention are particularly useful in the production of soft cheeses, which generally employ relatively small vats (typically from 200 to 1000 liters), which are refilled at very short intervals. Furthermore, an undesirable fermentation lag is particularly acute in production system when producing starter cultures.

The apparatus described in FIG. 1 allows a defined preactivation time for the DVS culture inoculated into the cheese vat or fermentation unit. The unit is constructed as a closed hygienic unit, which allows semi-continuous control and in-line dosage of the pre-activated culture. An additional feature by the disclosed invention is as follows: because the preincubation of the activated culture composition according to the invention takes place only "on demand"—and because it is taking place inside a closed and hygienic inline system—the risk of contamination is significantly less than with "batch" types of system.

According to a third aspect of the invention products are disclosed which are prepared according to the method provided above. Under this aspect, products which may be prepared according to the invention comprise dairy products such as e.g. hard cheeses comprising e.g. Cheddar and Emmental; semi-hard cheeses comprising e.g. Gouda, Tilsit, Danbo, Mozzarella and Raclette; soft cheeses comprising e.g. Brie, Camembert, Cresenza and Feta; and fermented products comprising e.g. set yoghurt and buttermilk.

In a fourth aspect the invention relates to compositions comprising the products according to the third aspect.

In a fifth aspect the invention relates to the use of such products and/or compositions according to the third and fourth aspects.

In a sixth aspect the invention relates to products and compositions that are produced by means of an apparatus according to the second aspect and by a method according to the first aspect.

The designations in FIG. 1 are to be understood as follows:

1: Vessel
2: Inlet hopper
3: Water inlet
4: Water jacket
5: Inlet for cooling water
6: Outlet for cooling water
7: Paddle
8: Load cell
9: Temperature sensor
10: Outlet valve
11: Pump
12: Conduit
13: Pump
14: Conduit
15: Inlet, pasteurised milk
16: Plate Heat Exchanger
17: Plate Heat Exchanger
18: Water inlet
19: Water outlet
20: In-line mixer
21: In-line tubular holding cell
22: Inlet, warm water
23: Outlet, warm water
24: In-line holding cell
25: Dosing valve
26: Dosing/dispensing nozzle
27: Cheese vat It is to be understood that the embodiments and variations shown and described herein are merely illustrative of the principles of this invention and that various modifications may be implemented by those skilled in the art without departing from the scope and spirit of the invention.

What is claimed is:

1. A method of preparing a dairy product, comprising the steps of:
   a) preparing an aqueous suspension of a dried or frozen microbial starter culture in a pasteurised or sterile water;
   b) mixing a metered flow of the aqueous suspension with a metered flow of milk, to form a starter culture composition;
   c) passing the starter culture composition through a pre-incubator, in which the starter culture composition is maintained at a preincubation temperature which is greater than about 10°C. but not sufficiently high as to have a deleterious effect on the microbial culture, wherein the residence time of the starter culture composition in the pre-incubator is such as to pre-activate the starter culture composition to form an activated culture composition;
   d) dispensing the activated culture composition and an additional quantity of milk into a fermentation vat to provide a fermentation mixture; and
   e) maintaining the fermentation mixture under fermentation conditions to obtain the dairy product.

2. A method as claimed in claim 1, wherein the pre-incubator is tubular.

3. A method as claimed in claim 1, wherein the residence time of the starter culture composition in the pre-incubator is from about 10 to about 60 minutes.

4. A method as claimed in claim 3, wherein the residence time of the starter culture composition in the pre-incubator is from about 10 to about 30 minutes.

5. A method as claimed in claims 1, 2 or 4, wherein the preincubation temperature is from about 10 to about 50°C.

6. A method as claimed in claim 5, wherein the preincubation temperature is from about 20° to about 45°C.

7. A method as claimed in claims 1, 2 or 4, wherein the preparation of the aqueous suspension in step (a) is carried out at a temperature of less than or equal to about 20°C.

8. A method as claimed in claims 1, 2 or 4, wherein the preparation of the aqueous suspension in step (a) is carried out at a temperature of less than or equal to about 15°C.

9. A method as claimed in claims 1, 2 or 4, wherein said mixing is carried out at the preincubation temperature.

10. A method as claimed in claims 1, 2 or 4, wherein the temperature of the pre-incubator is maintained by surrounding the pre-incubator with a heated fluid.

11. A method as claimed in claims 1, 2 or 4, wherein the activated culture composition is dispensed at intervals of 5 minutes or less.

12. A method as claimed in claim 11, wherein the activated culture composition is dispensed at intervals of 1 minute or less.

13. A method as claimed in claim 5, wherein the preincubation temperature is from about 30 to about 35°C.

14. A method as claimed in claim 1, wherein the pre-incubator is an in-line pre-incubator.

15. A method as claimed in claim 1, wherein the pre-incubator comprises a vessel, a tank or a vat.

16. A method as claimed in claim 2, wherein the residence time of the starter culture composition in the pre-incubator is from about 10 to about 60 minutes.

17. A method as claimed in claim 4, wherein the pre-incubator is tubular.

* * * * *